Feb. 23, 1960 J. E. MATEK Plant Pat. 1,918
AZALEA PLANT
Filed April 2, 1959
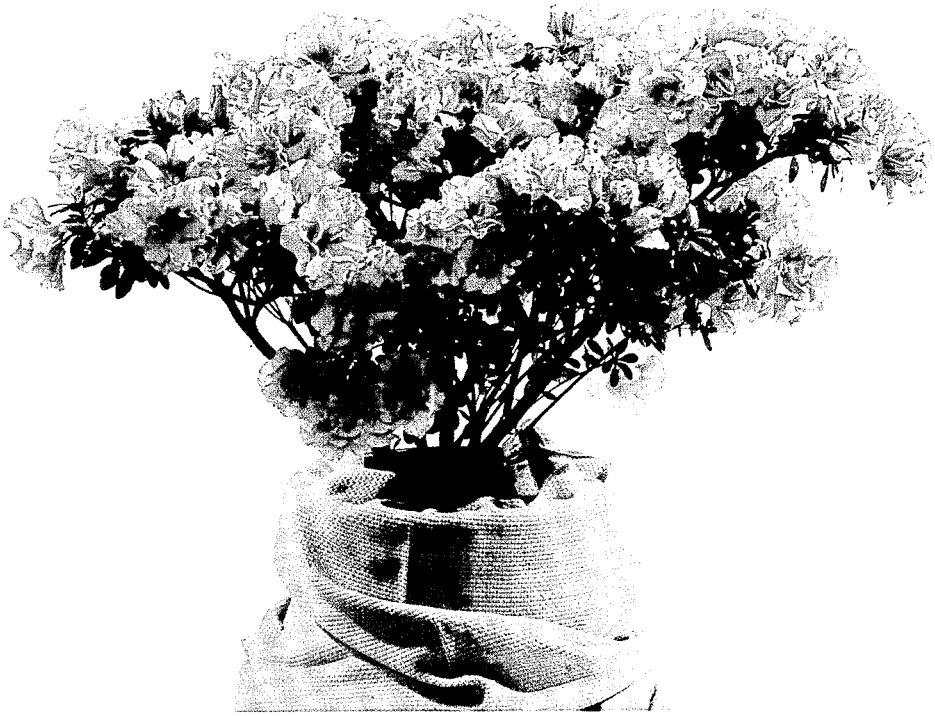

United States Patent Office

Plant Pat. 1,918
Patented Feb. 23, 1960

1,918

AZALEA PLANT

Jacob E. Matek, Oakland, Calif.

Application April 2, 1959, Serial No. 803,811

1 Claim. (Cl. 47—60)

The present invention relates to a new and distinct variety of azalea plant of the Belgian Indicum type, which was discovered by me by cross pollination between Fred Sanders (male parent, unpatented) and Eric Schame (female parent, unpatented). At the time of my initial discovery I was growing about 715 azalea plants from seed in the greenhouse of my property at Oakland, California. All of these plants were then placed in beds outside my greenhouse but still on my property and left to grow until some of them set bud. I then took about 150 of the budded azalea plants and placed then in my greenhouse to protect them from the weather until they flowered. When checking the flowers of the various plants in my greenhouse I discovered this particular azalea plant and noticed that its flowers had unusual color, which, to my knowledge had never appeared on any other azalea flower.

I immediately took steps to preserve this flower and plant and kept it under observation until it grew large enough to take cuttings. I then took cuttings of this azalea plant and asexually reproduced the same. I continued to observe the azalea plant and asexual reproductions thereof as performed by me by both grafting and cuttings in my greenhouse and noticed that the flowers of these asexually reproduced azalea plants were definitely different from their parents and were also different from all other varieties of which I was aware, while apparently falling in the general class, Indian azaleas (var. *R. indicum*) of the Belgian type.

This azalea plant is particularly characterized as to novelty by a unique combination of outstanding features, which include the following:

(1) Very distinctive rose pink color tonality of the flowers with a speckled Crimsom Glory throat;

(2) Vigorous and compact habit of growth, and very hardy;

(3) Heavy flower texture with ruffled petals; good keeping quality of the flowers;

(4) Persistent foliage;

(5) Excellent forcing stock.

*Drawing*

The accompanying color photograph in duplicate shows a typical specimen azalea plant of my new variety as depicted in color as nearly true as it is reasonably possible to make the same in a colored photograph of this character.

*Detailed description*

The following is a detailed description of the new variety of azalea plant with color terminology in accordance with Plochere Color System—"A Guide to Color and Color Harmony," by Gladys and Gustave Plochere, copyright 1948, except where general color terms of ordinary dictionary significance are obvious:

(Observations made from specimens grown in the greenhouse on my property at Oakland, California.)

*Propagation*

The azalea plant holds its distinctive characteristics through succeeding propagations by cutting or grafting and is excellent for forcing.

*Growth*

The azalea plant is vigorous and rapid in growth and is very compact.

*Blooming habit*

The blooms or flowers on the azalea plant are so profuse as to practically conceal the foliage. The plant usually blooms from December of one year through March of the following year.

*Foliage*

Foliage is persistent.

*Size (mature).*—Length—from about 1½ to 2 inches. Width—from about ¾ to 1 inch.

*Shape.*—Ovate.

*Quantity.*—Heavy, due to compact growth.

*Texture.*—Firm, smooth, glossy, similar to the female parent, Eric Schame (unpatented).

*Margin.*—Smooth.

*Color.*—Old foliage: upper side—Oak Leaf—Plate 48 (color #1137); under side—Fern Green—Plate 48 (#1131). New foliage: upper side—Green Moss—Plate 47 (#1122); under side—Piquant Green—Plate 47 (#1123).

*Flowers*

*Borne.*—Usually 2 flowers per bud sheath.

*Quantity.*—Free-flowering like female parent, Eric Schame (unpatented).

*Continuity.*—One heavy crop per season.

*Size.*—Approximately 3 to 4 inches in diameter.

*Petalage*

*Form.*—Semi-double, ruffled; the back petal is five-pointed; center petals have 6–9 points. Most blooms have functional pistils, a few have an incomplete complement of partially developed stamens.

*Texture.*—Heavy, hardy and long-lasting.

*Color new blossom.*—Rose Glory—Plate 15 (#340); fading gradually to Flamingo Pink—Plate 15 (#343), with a speckled Crimsom Glory throat—Plate 17 (#385); and finally fading to a Fuchsia Color—Plate 17 (#386).

*Bud*

*Form.*—Pointed.

*Color.*—Similar to newly opened flower—Rose Glory—Plate 15 (#340).

*Reproductive organs*

*Styles.*—About 1½ inches long of the same color as the newly opened blossom—Rose Glory—Plate 15 (#340), with antique gold stigma.

*Stamens.*—When present, are the same color as the styles—Rose Glory—Plate 15 (#340), with black anthers. The stamens are shorter than the styles and are quite attractive.

I claim:

A new and distinct variety of azalea plant of the Belgian Indicum type, substantially as herein shown and described, characterized particularly as to novelty by its very distinctive Rose Glory (Plate 15, #340) color tonality of its flowers, with a speckled Crimson Glory throat, vigorous and very compact habit of growth, persistent foliage, heavy texture and excellent keeping quality of the flowers, and excellent suitability for forcing.

No references cited.